(12) United States Patent
Ljungström et al.

(10) Patent No.: US 11,116,861 B2
(45) Date of Patent: *Sep. 14, 2021

(54) DEVICE FOR WASHING, DISINFECTING AND/OR STERILIZING MEDICAL, DENTAL, LABORATORY AND/OR PHARMACEUTICAL GOODS AND METHODS AND PROGRAM PRODUCTS FOR USE THEREIN

(71) Applicant: GETINGE STERILIZATION AB, Getinge (SE)

(72) Inventors: Hanna Ljungström, Gothenburg (SE); Per Norlin, Torslanda (SE)

(73) Assignee: GETINGE STERILIZATION AB, Getinge (SE)

(*) Notice: Subject to any disclaimer, the term of this patent is extended or adjusted under 35 U.S.C. 154(b) by 322 days.

This patent is subject to a terminal disclaimer.

(21) Appl. No.: 16/149,873

(22) Filed: Oct. 2, 2018

(65) Prior Publication Data

US 2019/0060499 A1 Feb. 28, 2019

Related U.S. Application Data

(62) Division of application No. 15/026,421, filed as application No. PCT/EP2013/070629 on Oct. 3, 2013, now Pat. No. 10,117,957.

(51) Int. Cl.
*A61L 2/24* (2006.01)
*G05B 19/409* (2006.01)
(Continued)

(52) U.S. Cl.
CPC .............. *A61L 2/24* (2013.01); *A61L 2/0005* (2013.01); *G05B 15/02* (2013.01); *G05B 19/409* (2013.01);
(Continued)

(58) Field of Classification Search
CPC ...... A61L 2/24; A61L 2/0005; A61L 2202/24; G05B 15/02; G05B 19/409;
(Continued)

(56) References Cited

U.S. PATENT DOCUMENTS 5,258,921 A 11/1993 Ellis
2007/0041864 A1* 2/2007 Forsyth .................... A61L 2/24
422/1

FOREIGN PATENT DOCUMENTS

CA 2437426 A1 2/2005
EP 1882479 A1 1/2008
(Continued)

OTHER PUBLICATIONS

English translation of JP-2008200126-A (Year: 2008).*
(Continued)

*Primary Examiner* — Regina M Yoo

(57) ABSTRACT

Devices having user-interactive guided control interfaces. The devices are for washing, disinfecting and/or sterilizing medical, dental, laboratory and/or pharmaceutical goods. Devices may include sterilizers, washer-disinfectors, autoclaves, and washers. Users are only presented with user interface objects which are appropriate at each step or process state of the guided process. Devices may include a touch screen, a chamber for goods to be processed, and a
(Continued)

door to the chamber. Different sets of user interface objects are presented on a display for different respective states of the device.

21 Claims, 4 Drawing Sheets

(51) Int. Cl.
*A61L 2/00* (2006.01)
*G05B 15/02* (2006.01)
*G06F 3/0481* (2013.01)
*G06F 3/0484* (2013.01)

(52) U.S. Cl.
CPC ...... *G06F 3/04817* (2013.01); *G06F 3/04842* (2013.01); *A61L 2202/24* (2013.01); *G05B 2219/2644* (2013.01); *G05B 2219/45169* (2013.01)

(58) Field of Classification Search
CPC .. G05B 2219/2644; G05B 2219/45169; G06F 3/04817; G06F 3/04842
See application file for complete search history.

(56) References Cited

FOREIGN PATENT DOCUMENTS

| EP | 2340853 A1 | 7/2011 | |
|---|---|---|---|
| JP | 2008-200126 A | 9/2008 | |
| JP | 2008200126 A * | 9/2008 | ............... A61L 2/24 |
| JP | 2010017411 A | 1/2010 | |
| WO | 2007021696 A2 | 2/2007 | |

OTHER PUBLICATIONS

Japanese Office Action (English translation) dated Nov. 14, 2017 for corresponding Japanese Patent Application No. 2016-546149, 2 pages.
Chinese Office Action and Chinese Search Report (both Chinese and English translations) dated Feb. 14, 2017 for corresponding Chinese Patent Application No. 201410310212.X, 20 pages.
International Search Report for Application No. PCT/EP2013/070629 dated Jan. 8, 2014.
International Preliminary Report on Patentability, Chapter II, for Application No. PCT/EP2013/070629 dated Feb. 2, 2016.
Examination report dated Sep. 2, 2020 in corresponding Indian Application No. 201617009946, 6 pages.

* cited by examiner

DEVICE FOR WASHING, DISINFECTING AND/OR STERILIZING MEDICAL, DENTAL, LABORATORY AND/OR PHARMACEUTICAL GOODS AND METHODS AND PROGRAM PRODUCTS FOR USE THEREIN

RELATED APPLICATIONS

Benefit and priority of parent U.S. application Ser. No. 15/026,421, now U.S. Pat. No. 10,117,957, is claimed. Benefit and priority of PCT/EP2013/070629 is also claimed.

TECHNICAL FIELD

Embodiments herein relate to devices for washing, disinfecting and/or sterilizing medical, dental, laboratory and/or pharmaceutical goods. In particular, embodiments herein relate to a device for washing, disinfecting and/or sterilizing medical, dental, laboratory and/or pharmaceutical goods. Also, embodiments herein relate to a method, device and a computer program product for use in a device for washing, disinfecting and/or sterilizing medical, dental, laboratory and/or pharmaceutical goods.

BACKGROUND

The pharmaceutical industry, hospitals, care centers, laboratories and similar industries and facilities are constantly struggling against contaminations. Hygiene issues are constantly on the agenda and continuously evaluated. One hygiene issue of special significance is the cleaning and sterilization of objects, such as reusable, consumable, and disposable equipment or goods. For example, a pharmaceutical production site may be equipped with steam generators, water pretreatment apparatuses, central sterile services, CPS, systems, CPS discharge systems, component washers, glassware washers, terminal sterilization systems, isolators and sterility testing equipment, simply to clean and sterilize different goods.

Reusable equipment can be surgical equipment such as knives, graspers, clamps, retractors, dialators, probes, scopes, drills, and saws, and laboratory equipment such as bottles, bowls, condensers, funnels, flasks, pipettes and plates, or the like. Any object which is intended to be reused and which can be contaminated with hazardous or biological substances is the subject of stringent hygiene conditions. Whenever reusable equipment has been used, the reusable equipment is sent for cleaning or sterilization.

Any piece of medical, dental, laboratory and/or pharmaceutical goods and/or equipment, which is intended to be used or re-used under the conditions described above, needs to be washed, disinfected and/or sterilized. Further, biohazardous material is in some cases also sterilized before being disposed of.

The process of washing, disinfecting and/or sterilizing goods, such as, e.g. medical, dental, laboratory and/or pharmaceutical goods and/or equipment mentioned above, is a highly demanding process in terms of the facilities used, the staff, the process parameters, the apparatuses and even the ambient environment surrounding the apparatuses. All restrictions and conditions serving the purpose to reduce, or eliminate, the risk for contamination makes it difficult and costly to operate such cleaning and sterilization processes.

SUMMARY

It is an object of embodiments herein to make the cleaning and sterilization processes more efficient and/or less costly.

According to a first aspect of embodiments herein, the object is achieved by a method performed by a device for washing, disinfecting and/or sterilizing medical, dental, laboratory and/or pharmaceutical goods in order to guide a user of the device through a process of operating the device. The device comprises at least one display for displaying a predetermined number of graphical interactive user interface objects, and a chamber for receiving said goods. The device detects a current first process state of the device. Then, the device indicates on the display a first set of said graphical interactive user interface objects associated with the detected current first process state visually differentiated from the other graphical interactive user interface objects of said graphical interactive user interface objects, with which first set of graphical interactive user interface objects the user interacts in order to cause the process of operating the device to change from the detected current first process state to a second process state.

According to a second aspect of embodiments herein, the object is achieved by a device for washing, disinfecting and/or sterilizing medical, dental, laboratory and/or pharmaceutical goods configured to guide a user of the device through a process of operating the device. The device comprises a chamber for receiving said goods and at least one display for displaying a predetermined number of graphical interactive user interface objects. The device further comprises processing circuitry configured to detect a current first process state of the device, and to indicate on the display a first set of said graphical interactive user interface objects associated with the detected current first process state visually differentiated from the other graphical interactive user interface objects of said graphical interactive user interface objects, with which first set of graphical interactive user interface objects the user interacts in order to cause the process of operating the device to change from the detected current first process state to a second process state.

According to a third aspect of embodiments herein, the object is achieved by a computer program product for guiding a user of a device for washing, disinfecting and/or sterilizing medical, dental, laboratory and/or pharmaceutical goods through a process of operating the device. The device comprises a chamber for receiving said goods, a display for displaying a predetermined number of graphical interactive user interface objects, and processing circuitry. The computer program product comprises code instructions configured for execution by the processing circuitry and which code instructions when executed in the device causes the device to: detect a current first process state of the device, and to indicate on the display a first set of said graphical interactive user interface objects associated with the detected current first process state visually differentiated from the other graphical interactive user interface objects of said graphical interactive user interface objects, with which first set of graphical interactive user interface objects the user interacts in order to cause the process of operating the device to change from the detected current first process state to a second process state.

By detecting the current process state of the device and indicating, to a user of the device, graphical interactive user interface objects on a display that are visually differentiated from other graphical interactive user interface objects based on the detected current process state, the user is directly confronted with ways of operating the device that will result in a more efficient, intuitive and safe handling of the device and the goods therein. That is, by displaying only what is necessary for leading the user into the next process state, the user is visually and intuitively guided through the process of operating the device in an effective and secure manner.

This simplifies the handling of the device in a manner that will make the cleaning and sterilization processes of medical, dental, laboratory and/or pharmaceutical goods more efficient and/or less costly.

BRIEF DESCRIPTION OF THE DRAWINGS

Features and advantages of the embodiments will become readily apparent to those skilled in the art by the following detailed description of exemplary embodiments thereof with reference to the accompanying drawings, wherein.

DETAILED DESCRIPTION

Figure 1:
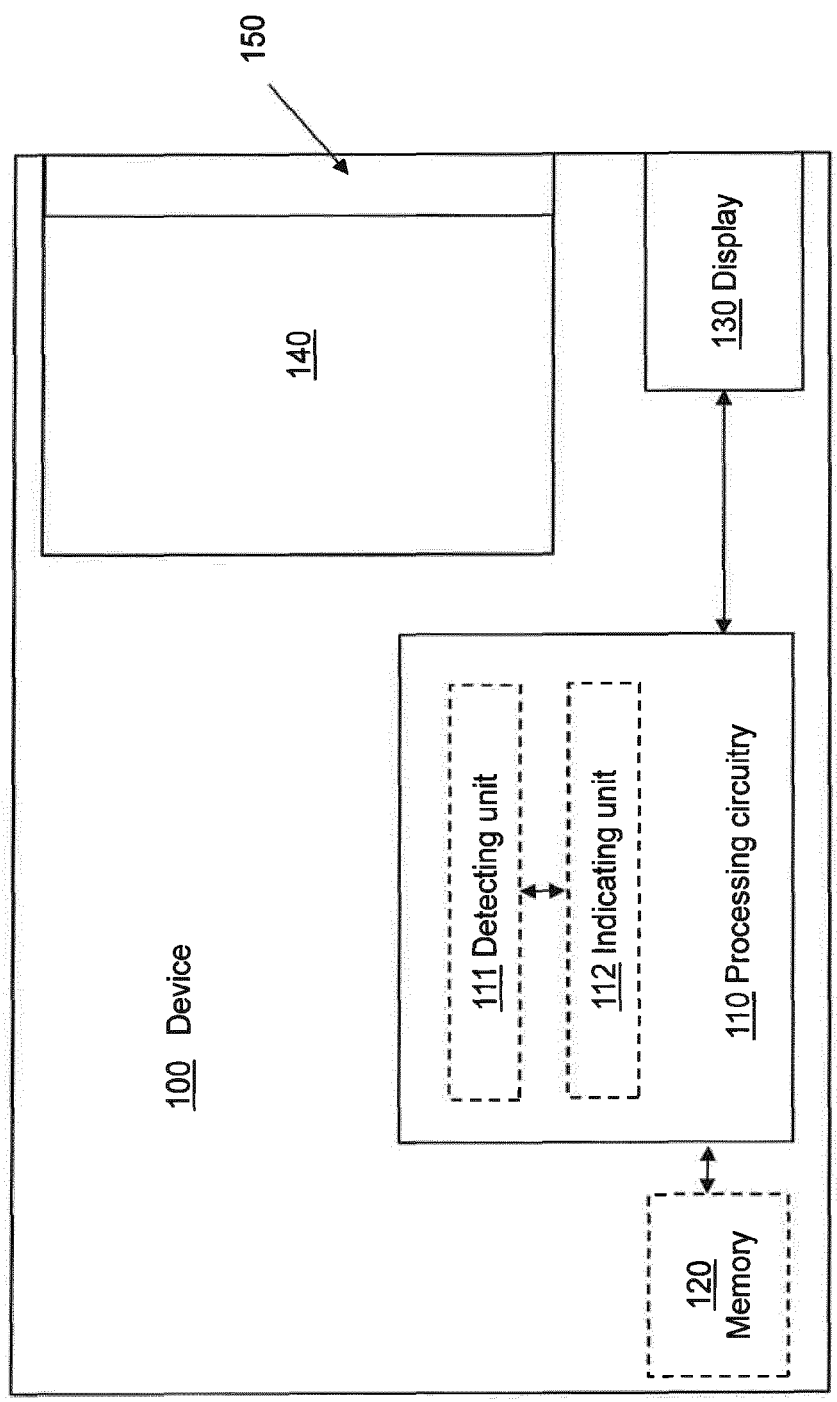
FIG. 1 is a schematic block diagram depicting embodiments of a device for washing, disinfecting and/or sterilizing medical, dental, laboratory and/or pharmaceutical goods.

Non-limiting embodiments of the present disclosure will now be described more fully hereinafter with reference to the accompanying drawings, in which currently preferred embodiments of the disclosure are shown. This disclosure may, however, be embodied in many different forms and should not be construed as limited to the embodiments set forth herein. Like reference characters refer to like elements throughout. Dashed lines of some boxes in the figures indicate that these units or actions are optional and not mandatory.

As part of understanding the embodiments described herein, a problem will first be identified and discussed in more detail.

It has been noted that operating a device for washing, disinfecting and/or sterilizing medical, dental, laboratory and/or pharmaceutical goods today often leaves a user struggling or uncomfortable with how to proceed through the process of operating the device. This also follows from the fact that, if the device is not properly operated, it may lead to the goods not being properly sterilized or disinfected, or even damaged.

Furthermore, it has also been noted that current graphical user interfaces (GUIs) of these devices do not provide any support to the user of the devices in achieving an efficient work flow when using them. In fact, users that have problems handling the GUI of the device are a primary cause of the work flow when using the devices slowing down. This will cause or increase the number of goods waiting to be sterilized or disinfected, and consequently cause or increase the queue of goods and delay in arrival of sterilized or disinfected goods.

These issues are addressed and essentially alleviated by the embodiments described herein.

In the following, according to embodiments herein which relate to guiding a user through a process of operating a device for washing, disinfecting and/or sterilizing medical, dental, laboratory and/or pharmaceutical goods, there will be disclosed how the device detects a current first process state which the device is in at a given moment, and then indicates, to the user of the device, graphical interactive user interface objects which display what is necessary for leading the user to the next process state in an effective and secure manner. This may also comprise suppressing graphical user interface objects and/or graphical interactive user interface objects which are not relevant for the detected current first process state. Thus, a contextual guidance through each process state in the process of operating the device is provided.

Referring now to the drawings and FIG. 1 in particular, there is depicted a schematic block diagram illustrating a device 100 for washing, disinfecting and/or sterilizing medical, dental, laboratory and/or pharmaceutical goods (not shown). The device 100 may according to embodiments herein comprise an autoclave, a washer, a washer disinfector, or a drying cabinet. The device 100 comprises a chamber 140 for receiving the goods, and at least one openable door 150 associated with the chamber 140.

The device 100 furthermore comprises at least one display 130, which display 130 may be a touch screen or touch sensitive display, such as, e.g. a multi-touch sensitive display. In some embodiments, the display 130 may be physically connected and mounted to the device 100 (as shown in FIG. 1). In some embodiments, the display 130 may be remotely connected to the device 100, e.g. via a wire or a wireless connection. The latter may be performed over a wireless network to which both the display 130 and the device 100 may be connected, such as, e.g. a WiFi network or the like, or over a direct wireless connection between the display 130 and the device 100, such as, e.g. Bluetooth or the like. Also, the display 130 may here be comprised in a wireless communication device, such as, a mobile terminal or wireless terminal (such as, e.g. a mobile telephone, cellular telephone, smart phone) or a computer (such as, e.g. a laptop, Personal Digital Assistants (PDAs) or tablet computer with wireless capability).

Furthermore, the embodiments herein for guiding a user through a process of operating a device 100 for washing, disinfecting and/or sterilizing medical, dental, laboratory and/or pharmaceutical goods may be implemented through processing circuitry 110, together with computer program code for performing the functions and actions of the embodiments herein. Said program code may also be provided as a computer program product, for instance in the form of a data carrier carrying computer program code for performing the embodiments herein when loaded into the device 100. One such data carrier may be in the form of a CD ROM disc. It is, however, feasible with other data carriers such as, for example, a hard drive, a semiconductor memory, a flash memory stick, etc. The computer program code may furthermore be provided as pure program code on a server and downloaded to the device 100. The device 100 may further comprise a memory 120 comprising one or more memory units. The memory 120 may be arranged to be used to store e.g. information, and further to store data and applications, to perform the methods herein when being executed in the device 100. The memory 120 and the processing circuitry 110 may for instance be implemented in one or several control units. Those skilled in the art will also appreciate that the processing circuitry 110, which for instance may comprise a detecting unit 111 and an indicating unit (or display unit) 112, may refer to a combination of analog and digital circuits, and/or one or more processors configured with software and/or firmware, e.g. stored in a memory such as the memory 120, that when executed by the one or more processors perform as will be described in more detail later on in this description.

One or more of these processors, as well as the other digital hardware, may be included in a single ASIC (Application-Specific Integrated Circuitry), or several processors and various digital hardware may be distributed among several separate components, whether individually packaged or assembled into a SoC (System-on-a-Chip).

Figure 2:
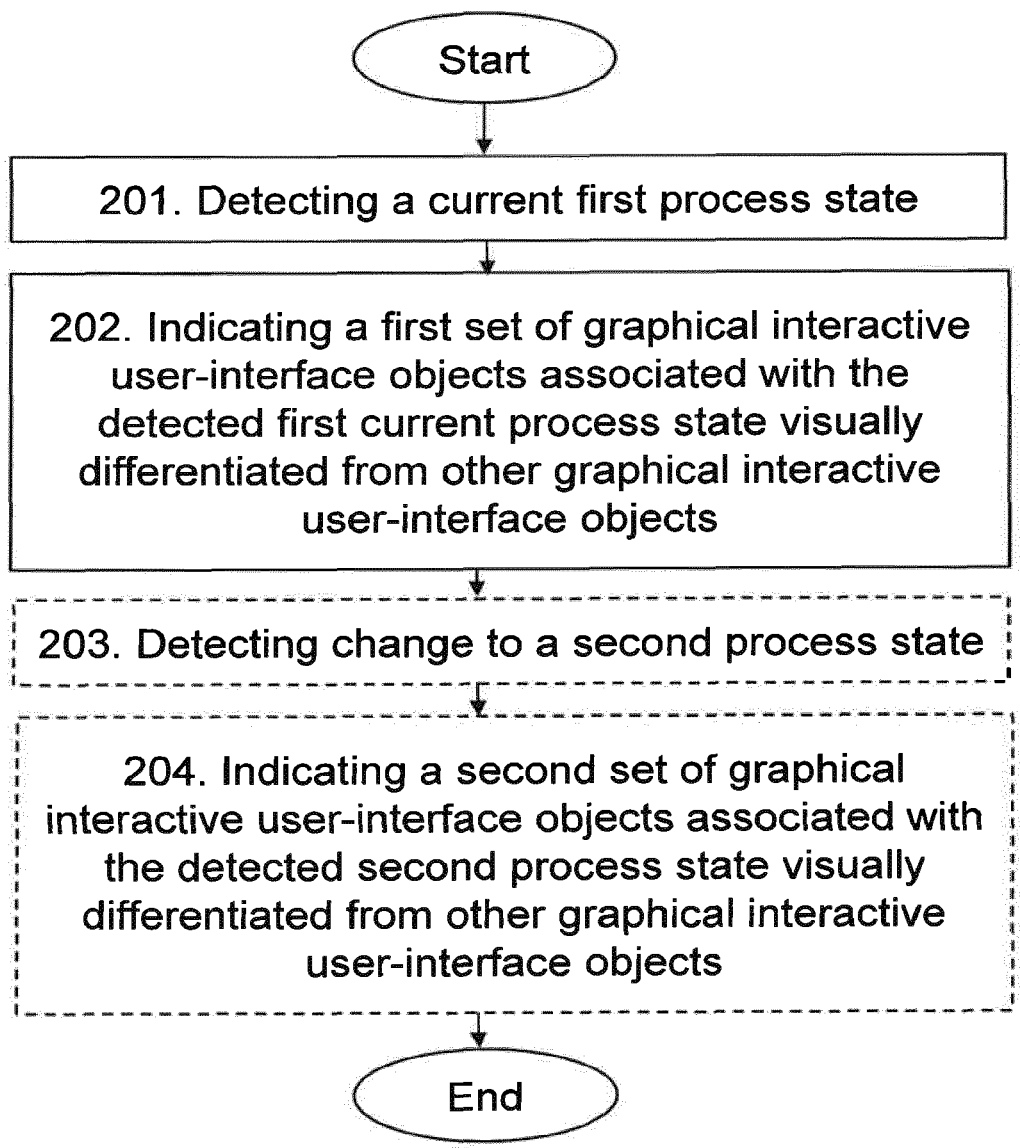
FIG. 2 is a flowchart depicting embodiments of a method performed by a device for washing, disinfecting and/or sterilizing medical, dental, laboratory and/or pharmaceutical goods in order to guide a user of the device through a process of operating the device.

FIG. 2 is a flowchart depicting a method for guiding a user through a process of operating a device 100 for washing, disinfecting and/or sterilizing medical, dental, laboratory and/or pharmaceutical goods, according to embodiments of the disclosure. The method comprises the following actions discussed with support from FIG. 1. The actions may be taken in any suitable order, and when applicable, taken in parallel.

Action 201

In this action, the device 100 detects, e.g. by means of the detecting unit 111, the current process state of the device 100. As non-limiting examples, a process state of the device 100 in the process of operating the device 100, may be one of the following:
- stand-by, e.g. when no goods have been loaded in the device and no program has been selected,
- door open, e.g. a user has opened the door in order to load the goods to be sterilized or disinfected into the chamber 140,
- door closed, e.g. user has closed the door after loading the goods to be sterilized or disinfected into the chamber 140,
- door stuck, e.g. due to improper loading of the goods in the chamber 140,
- program selected, e.g. the user has chosen a program to be performed by the device 100,
- program edit, e.g. the user has chosen to adjust one or more parameters of the program,
- program started, e.g. the device 100 has started washing, sterilizing or disinfecting the goods according to the user selected program,
- program complete, e.g. the device 100 has finished washing, sterilizing or disinfecting the goods according to the user selected program.

Further non-limiting examples of process states may comprise one or more alarm process states or warning process states, e.g. due to improper functioning of the device 100, or cancel process states, e.g. when the user has chosen to interrupt an on-going process. Some of these non-limiting examples of process states are described further with reference to FIG. 3 below. The process states of the device 100 may also be referred to as machine or device states.

In some embodiments, the detection of the current process state of the device 100, e.g. by means of the detecting unit 111, is performed in response to a user interaction with the device 100 via one or more of the graphical interactive user interface objects of the first set of graphical interactive user interface objects. This may, for example, occur when the touch sensitive display 130 detects a contact with an area on the touch sensitive display 130 corresponding to one or more of the graphical interactive user interface objects of the first set of graphical interactive user interface objects. One example of this may be when the user of the device 100 contacts the touch sensitive display 130 in order to select a program of the device 100.

Alternatively, the detection of the current process state of the device 100, e.g. by means of the detecting unit 111, is performed in response to a detected change in the operation of the device 100 by the device 100 itself. This may, for example, occur when the door is opened or closed by the user of the device 100, or when the device 100 has finished sterilizing or disinfecting the goods according to a user selected program.

Action 202

Following the detection of the current process state, the device 100 indicates, e.g. by means of the indicating unit (or display unit) 112, on the display 130 a first set of said graphical interactive user interface objects associated with the detected current first process state visually differentiated from the other graphical interactive user interface objects of said graphical interactive user interface objects. With this first set of graphical interactive user interface objects the user interacts in order to cause the process of operating the device 100 to change from the detected current first process state to a second process state. In other words, these first set of graphical interactive user interface objects are allowed by the device 100 in the detected current first process state since a user interaction with these first set of graphical interactive user interface objects will cause the process of operating the device 100 to change from the detected current first process state to a second process state.

Hence, the transition into the second process state may be controlled in an efficient and safe manner since the user may be directly confronted, via the first set of graphical interactive user interface objects, with limited ways of operating the device 100. This also means that graphical interactive user interface objects which do not lead to a transition into the second process state in a safe and efficient manner or is irrelevant to the first process state will be visually differentiated, e.g. not displayed, from the first set of graphical interactive user interface objects on the display 130.

This means that the user of the device 100 is only confronted with information necessary at the current process state. Thus, advantageously, the user of the device 100 does not have to navigate through the system, e.g. via different menu's, windows or tabs, in order to have the required information displayed. Consequently, a more user-friendly graphical user interface (GUI) providing an improved Human-to-Machine Interface (HMI) is provided.

Here, it should be noted that the second process state may be a subsequent or following process state with reference to the current first process state in the process of operating the device 100.

Action 203

In this optional action 203, the device 100 may detect, e.g. by means of the detecting unit 111, that the process of operating the device 100 has changed to a second process state.

In some embodiments, the detection of the change of current process state of the device 100, e.g. by means of the detecting unit 111, is performed in response to a user interaction with the device 100 via one or more of the graphical interactive user interface objects of the first set of graphical interactive user interface objects. Alternatively, the detection of the change of current process state of the device 100, e.g. by means of the detecting unit 111, is performed in response to a detected change in the operation of the device 100 by the device 100 itself.

Action 204

In response to detecting the change in Action 203, the device 100 may indicate, e.g. by means of the indicating unit (or display unit) 112, on the display 130 a second set of graphical interactive user interface objects associated with the detected second process state visually differentiated from the other graphical interactive user interface objects of said graphical interactive user interface objects. With this second set of graphical interactive user interface objects the user interacts in order to cause the process of operating the device 100 to change from the detected second process state to a further process state.

In other words, this second set of graphical interactive user interface objects are the graphical interactive user interface objects that are allowed for the user of the device 100 to interact with during the detected second process state. This second set of graphical interactive user interface objects are allowed by the device 100 in the detected second process state in order to, upon a user interaction with this second set of graphical interactive user interface objects, cause the process of operating the device 100 to change from the current detected second process state to a third process state.

This implies that continuous transitions into the next desired process state may be controlled in an efficient and safe manner since the user may be directly confronted, via the second set of graphical interactive user interface objects, with limited ways of operating the device 100 from the detected current process state.

Here, also graphical interactive user interface objects which do not lead to a transition into the third process state in a safe and efficient manner will be visually differentiated, e.g. not displayed, displayed in a different color, displayed in a different size and/or shape, etc., from the second set of graphical interactive user interface objects on the display 130. For example, these graphical interactive user interface objects may be one or more graphical interactive user interface objects comprised in the first set of graphical interactive user interface objects.

This means that the user of the device 100 is only confronted with information necessary at each process state. Thus, advantageously, the user of the device 100 does not have to navigate through system, e.g. via different menus, windows or tabs, in order to have the required information for each process state displayed. Consequently, a more user-friendly graphical user interface (GUI) providing an improved Human-to-Machine Interface (HMI) is provided.

Here, it should be noted that the further process state may be a subsequent or following process state with reference to the current second process state in the process of operating the device 100.

Furthermore, in some embodiments, the first and second set of graphical interactive user interface objects may be visually differentiated from other graphical interactive user interface objects during the detected first and second process state, respectively, by one or more of the following:

displaying versus not displaying. For example, during the detected first or second process state, the graphical interactive user interface objects of the first or the second set of graphical interactive user interface objects, respectively, are indicated on the display 130, while other graphical interactive user interface objects are not displayed.

coloring versus non-coloring. For example, during the detected first or second process state, the graphical interactive user interface objects of the first or the second set of graphical interactive user interface objects, respectively, are indicated on the display 130 in color, while other graphical interactive user interface objects are displayed, not in color (e.g. displayed in black and white or grayscale only).

a first coloring versus at least one second coloring. For example, during the detected first or second process state, the graphical interactive user interface objects of the first or the second set of graphical interactive user interface objects, respectively, are indicated on the display 130 in a first color (e.g. blue), while other graphical interactive user interface objects are displayed in one or more second color (i.e. one or more colors other than blue).

shading versus non-shading. For example, during the detected first or second process state, the graphical interactive user interface objects of the first or the second set of graphical interactive user interface objects, respectively, are indicated on the display 130 using a shading to emphasize or enhance a graphical interactive user interface object (or to provide for a so-called 3D-effect of the graphical interactive user interface object), while other graphical interactive user interface objects are non-shaded.

a first display intensity versus at least one second display intensity. For example, during the detected first or second process state, the graphical interactive user interface objects of the first or the second set of graphical interactive user interface objects, respectively, are indicated on the display 130 using a first display intensity to emphasize or enhance the graphical interactive user interface objects, while other graphical interactive user interface objects are indicated on the display 130 using at least one second display intensity (e.g. a lower intensity than the first display intensity).

frames versus no frames. For example, during the detected first or second process state, the graphical interactive user interface objects of the first or the second set of graphical interactive user interface objects, respectively, are indicated on the display 130 using a frame to emphasize or enhance a graphical interactive user interface object, while other graphical interactive user interface objects do not have any frames.

a first font versus at least one second font. For example, during the detected first or second process state, the graphical interactive user interface objects of the first or the second set of graphical interactive user interface objects, respectively, are indicated on the display 130 using a first font on the text thereon to emphasize or enhance the graphical interactive user interface objects, while other graphical interactive user interface objects are indicated on the display 130 using at least one second font (e.g. a smaller or different font than the first font).

It should be noted that the examples of visually differentiation described above should not be construed as limiting to this disclosure, but to emphasize the principle of the embodiments herein.

The process of operating the device 100, in some embodiments, comprises a number of process states in each of which only a limited set of operations are allowed and relevant in the context of leading a user of the device 100 in transitioning the device 100 from one process state into another process state, e.g. from a first to a second process state or from the second to at least one further process state, etc., as described above. In these cases, each of the limited sets of operations of each process state may be associated with a corresponding set of graphical interactive user interface objects, e.g. the first set of graphical interactive user interface objects during the first process state or the second set of graphical interactive user interface objects during the second process state, etc.

Advantageously, this further provides for a more safe and efficient use of the device 100 in that, during certain process states, operations that are not allowed and relevant in the context of leading a user of the device 100 in transitioning the device 100 from one process state into another process state are not selectable or even displayed during these certain process states.

In some embodiments, the first and second set of graphical interactive user interface objects may be visually differentiated from other graphical, user interface objects during the detected first and second process state, respectively, by having a blue color.

This advantageously assigns a unique color for guiding the user of the device 100 through the process of operating the device 100 in a safe and effective manner. Other colors may then be used in order to indicate other scenarios (such as, e.g. the color red may be used to signal errors/alarms to the user of the device 100, the color yellow may be used to signal warnings to the user of the device 100, and/or the color green to only signal when a program has been successfully completed in the device 100) without confusion to the user of the device 100 of which way forward will lead to a safe transition from one process state into another process state.

In some embodiments, the blue color may, when represented by an RGB color code, comprise the color values of on or about 0:170:255. If comprising a gradient, the blue color may further comprise color values of on or about 37:59:126, when represented by an RGB color code. This distinctive coloring of a safe path forward in operating the device 100 is advantageous in that it provides an intuitive and user-friendly guide through the process of operating the device 100.

Figure 3:
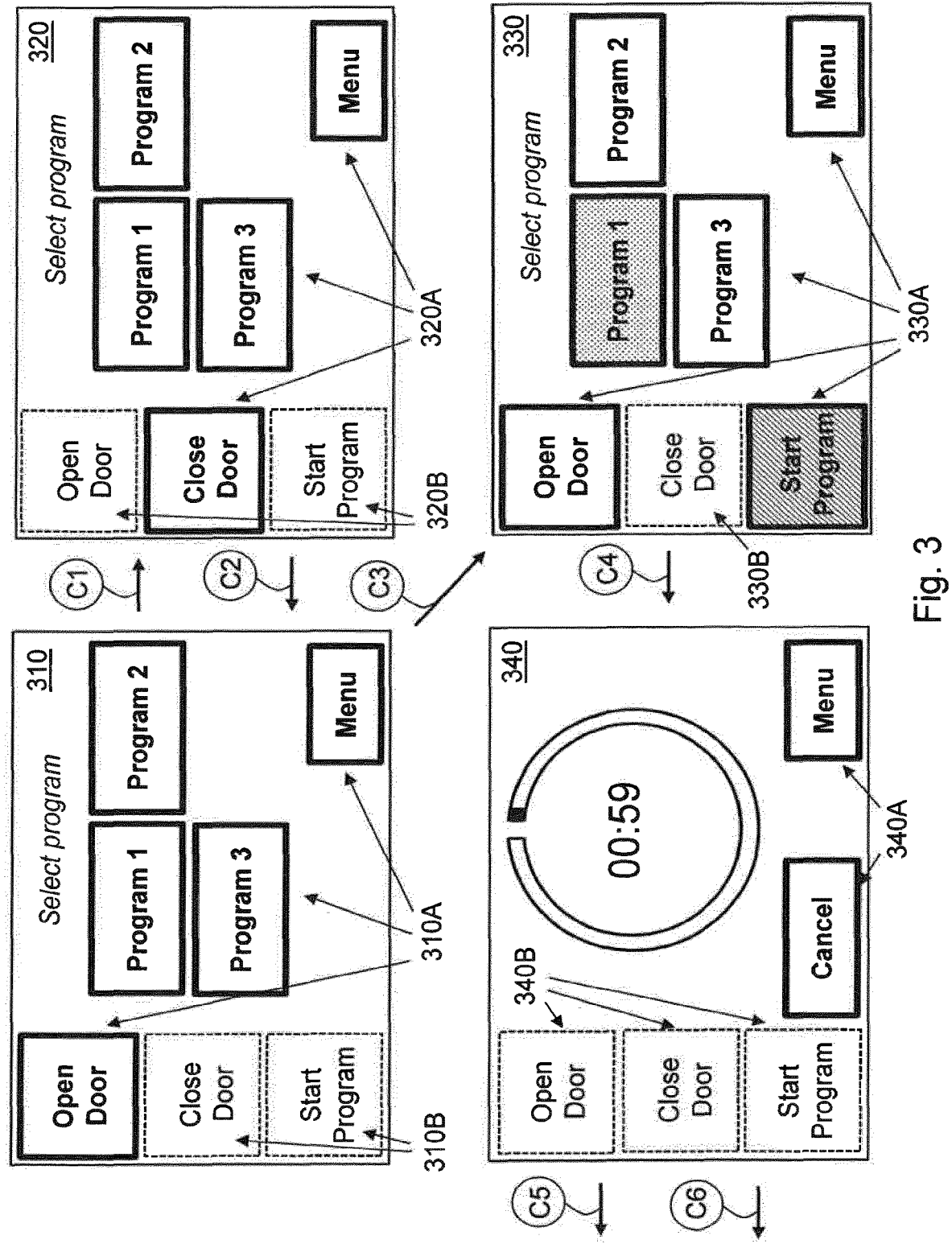
FIG. 3 shows exemplifying display views comprising graphical interactive user interface objects depicting embodiments of the device for washing, disinfecting and/or sterilizing medical, dental, laboratory and/or pharmaceutical goods.

FIG. 3 shows exemplifying display views 310, 320, 330, 340 of the display 130 comprising sets of graphical interactive user interface objects 310A, 310B, 320A, 320B, 330A, 330B, 340A, 340B according to some embodiments. It should be noted that the embodiments described below are simplified for more clearly demonstrating the principle of the embodiments described herein.

First View 310

This first view 310 may be shown during a detected stand-by process state or stand-by, such as, e.g. when no goods have been loaded into the device 100 and no program has yet been selected by the user of the device 100. This state may be detected e.g. upon starting or waking up the device 100.

In the simplified embodiment of FIG. 3, the device 100 is here configured, when being in the detected stand-by process state, to allow the user of the device 100 to perform the operation of opening the door or the operation of selecting a program of the device 100. The device 100 comprises a first set of graphical interactive user interface objects 310A which are associated with these allowed operations and the detected stand-by process state.

As shown in the first view 310, the first set of graphical interactive user interface objects 310A may comprise a graphical interactive user interface object, "Open door", being associated with the operation of opening the door 150, e.g. actually opening the door 150 or indicating to the user that the door 150 may be opened.

The first set of graphical interactive user interface objects 310A may also comprise a group of graphical interactive user interface objects, "Program 1", "Program 2", "Program 3", etc., being associated with different programs of operating the device 100. For example, in case the device 100 is a sterilization device, such as, e.g. an autoclave, the group of graphical interactive user interface objects, "Program 1", "Program 2", "Program 3", etc., may represent different sterilization programs differentiated by at least one parameter, such as, e.g. sterilization temperature, process cycle time, number of sterilization cycles, etc.

The first set of graphical interactive user interface objects 310A may also comprise a graphical interactive user interface object, "Menu", being associated with the operation of providing the user with more detailed information, such as, e.g. the current settings of the device 100, or further operations of the device 100. Note that, in some embodiments, some graphical interactive user interface objects, such as, e.g. the graphical interactive user interface object, "Menu", may be present in all or at least several sets of graphical interactive user interface objects. Thus, it should be noted that at least one graphical interactive user interface object may be indicated visually identical in a first and a second process state, and that this at least one graphical interactive user interface object need not be related to the current process state or transitions between different process states of the device 100, but rather related to current settings in the device 100 that are preferably almost always available.

It should also be noted that this does not exclude other graphical user interface objects of optional parameters or settings that are not related to the current process state or transitions between different process states of the device 100 to be presented throughout several or all process states. Examples of such parameters or settings may be a program temperature or program time.

In the first view 310, the device 100 indicates, e.g. by means of the indicating unit (or display unit) 112 on the display 130, the first set of graphical interactive user interface objects 310A visually differentiated from other graphical interactive user interface objects 310B. In this case, the other graphical interactive user interface objects 310B may comprise a graphical interactive user interface object, "Door closed", being associated with the operation of closing the door 150, and a graphical interactive user interface object, "Start program" being associated with the operation of starting a program of the device 100. This is because the device 100 is here configured, when being in the detected stand-by process state, to not allow the user of the device 100 to perform the operation of closing the door (since door is already closed) or the operation of starting a program of the device 100 (since no program has been selected and the device 100 is not in a process state yet that would enable a program to start).

However, it should also be noted that the other graphical interactive user interface objects 310B, in this case, also comprise all other graphical interactive user interface objects not being indicated in the first view 310.

As can be seen in the first view 310, the first set of graphical interactive user interface objects 310A are shown as clearly distinctive from the other graphical interactive user interface objects 310B by having heavily marked edges (as indicated by the fully drawn, heavy lines) and bold font, whereas the other graphical interactive user interface objects 310B are either not displayed or have faintly marked edges (as indicated by the dashed lines) and regular font. In some embodiments, the first set of graphical interactive user interface objects 310A may preferably comprise a blue color to some extent so as to guide the user in the manner previously described above.

This translates into the first set of graphical interactive user interface objects 310A being perceived as active, whereas the other graphical interactive user interface objects 310B being perceived as inactive. However, as previously described in embodiments above, many modifications and variations are possible for achieving the desired differentiation between the first set of graphical interactive user interface objects 310A and the other graphical interactive user interface objects 310B.

When in the stand-by process state, the device 100, e.g. by means of the detecting unit 111, may detect a change C1 in the current process state of the device 100 from the stand-by process state into another process state. In this example, this may e.g. be caused by a user interaction with the graphical interactive user interface object, "Open door", being associated with the operation of opening the door 150. Alternatively, the device 100 may detect that the door 150 has been opened.

Second View 320

This second view 320 may, for example, be shown during a detected door open state and in response to detecting the change C1.

In the simplified embodiment of FIG. 3, the device 100 is here configured, when being in the detected door open state, to allow the user of the device 100 to perform the operation of closing the door or the operation of selecting a program of the device 100. The device 100 comprises a second set of graphical interactive user interface objects 320A which are associated with these allowed operations and the detected door open state. Note that graphical interactive user interface objects comprised in the first set of graphical interactive user interface objects 310A may also be present in this second set of graphical interactive user interface objects 320A.

As shown in the second view 320, the second set of graphical interactive user interface objects 320A may comprise a graphical interactive user interface object, "Close door", being associated with the operation of closing the door 150, e.g. actually closing the door 150 or indicating to the user that the door 150 may be closed.

The second set of graphical interactive user interface objects 320A may also comprise the group of graphical interactive user interface objects, "Program 1", "Program 2", "Program 3", as previously described.

In the second view 320, the device 100 indicates, e.g. by means of the indicating unit (or display unit) 112 on the display 130, the second set of graphical interactive user interface objects 320A visually differentiated from other graphical interactive user interface objects 320B. In this case, the other graphical interactive user interface objects 320B may comprise the graphical interactive user interface object, "Open door", being associated with the operation of opening the door 150, and a graphical interactive user interface object, "Start program" being associated with the operation of starting a program of the device 100. This is because the device 100 is here configured, when being in the detected door open state, to not allow the user of the device 100 to perform the operation of opening the door or the operation of starting a program of the device 100. However, it should also be noted that the other graphical interactive user interface objects 320B, in this case, may also comprise all other graphical interactive user interface objects not being indicated in the second view 320.

As can be seen in the second view 320, the second set of graphical interactive user interface objects 320A are shown as clearly distinctive from the other graphical interactive user interface objects 320B by having heavily marked edges (as indicated by the fully drawn, heavy lines) and bold font, whereas the other graphical interactive user interface objects 320B are either not displayed or have faintly marked edges (as indicated by the dashed lines) and regular font. In some embodiments, the second set of graphical interactive user interface objects 320A may preferably comprise a blue color to some extent so as to guide the user in the manner previously described above.

This translates into the second set of graphical interactive user interface objects 320A being perceived as active, whereas the other graphical interactive user interface objects 320B are perceived as inactive. However, as previously described in embodiments above, many modifications and variations are possible for achieving the desired differentiation between the first set of graphical interactive user interface objects 320A and the other graphical interactive user interface objects 320B.

When in the door open state, the device 100, e.g. by means of the detecting unit 111, may detect a change C2 in the current process state of the device 100 from the door open state into another process state. In this example, this may e.g. be caused by a user interaction with the graphical interactive user interface object, "Close door", being associated with the operation of closing the door 150. Alternatively, the device 100 may detect that the door 150 has been closed. Hence, in this example, the other process state is here a door closed state. In some embodiments, the device 100 may then return to the first view 310, wherein the same conditions apply for the door closed state as described for the stand-by process state.

The device 100 may, e.g. by means of the detecting unit 111, also detect a change C3 in the current process state of the device 100 from the door closed state into another process state. In this example, this may e.g. be caused by a user interaction with one of the graphical interactive user interface object of the group of graphical interactive user interface objects, "Program 1", "Program 2", "Program 3", etc., being associated with different programs of operating the device 100. Hence, in this example, the other process state is here a program selected state. In the third view 330 described below, this is denoted by the graphical interactive user interface object, "Program 1", being dotted, i.e. as being selected by the user of the device 100.

Third View 330

This third view 330 may, for example, be shown during a detected program selected state and in response to detecting the change C3.

In the simplified embodiment of FIG. 3, the device 100 is here configured, when being in the detected program selected state, to allow the user of the device 100 to perform the operation of closing the door, selecting another program of the device 100 and starting the selected program of the device 100. The device 100 comprises a third set of graphical interactive user interface objects 330A which are associated with these allowed operations and the detected program selected state. Note that graphical interactive user interface objects comprised in the first or second set of graphical interactive user interface objects 310A, 320A may also be present in this third set of graphical interactive user interface objects 330A.

As shown in the third view 330, the third set of graphical interactive user interface objects 330A may comprise the graphical interactive user interface object, "Open door", being associated with the operation of opening the door 150, and the group of graphical interactive user interface objects, "Program 1", "Program 2", "Program 3", as previously described. In this third view 330, since being allowed in the detected program selected state, the third set of graphical interactive user interface objects 330A may comprise the graphical interactive user interface object, "Start program", being associated with the operation of starting a program of the device 100.

In the third view 330, the device 100 indicates, e.g. by means of the indicating unit (or display unit) 112 on the display 130, the third set of graphical interactive user interface objects 330A visually differentiated from other graphical interactive user interface objects 330B. In this example, the other graphical interactive user interface objects 330B may comprise the graphical interactive user interface object, "Close door", being associated with the operation of closing the door 150. Also, note that the other graphical interactive user interface objects 330B, in this case, may also comprise all other graphical interactive user interface objects not being indicated (displayed) in the third view 330.

As can be seen in the third view 330, the third set of graphical interactive user interface objects 330A are shown as clearly distinctive from the other graphical interactive user interface objects 330B by having heavily marked edges (as indicated by the fully drawn, heavy lines) and bold font, whereas the other graphical interactive user interface objects 330B are either not displayed or have faintly marked edges (as indicated by the dashed lines) and regular font. In some embodiments, the third set of graphical interactive user interface objects 330A may preferably comprise a blue color to some extent so as to guide the user as has been previously described above.

Alternatively, the device 100 may provide a default selection of a program that may be changed by the user by pressing an alternative program button, i.e. interacting with one of the graphical interactive user interface objects of the third set of graphical interactive user interface objects 330A, such as, e.g. "Program 2" or "Program 3". In that case, the selected program will change to the process program corresponding to the selected program button.

The above translates into the third set of graphical interactive user interface objects 330A being perceived as active, whereas the other graphical interactive user interface objects 330B are perceived as inactive. However, as previously described in embodiments above, many modifications and variations are possible for achieving the desired differentiation between the third set of graphical interactive user interface objects 330A and the other graphical interactive user interface objects 330B.

It should also be noted that graphical interactive user interface objects being associated with the special features, such as, e.g. starting a program of the device 100, "Start program", may be further differentiated from other graphical interactive user interface objects as shown in the third view 330 (denoted by the graphical interactive user interface object, "Start program", being dashed). In some embodiments, the graphical interactive user interface object, "Start program", may preferably comprise a blue color to some extent so as to guide the user onwards.

Here, it should be noted that during a detected program selected state and in response to detecting the change C3, other graphical user interface objects (not shown) of optional parameters or settings that are not related to the current process state or transitions between different process states of the device 100 may also to be presented here. For example, graphical user interface objects associated with program temperature or program time of the selected program may be presented, which may enable the user of the device 100 to visually confirm that the correct program parameters or settings are used.

When in program selected state, the device 100, e.g. by means of the detecting unit 111, may detect a change C4 in the current process state of the device 100 from the program selected state into another process state. In this example, this may e.g. be caused by a user interaction with the graphical interactive user interface object, "Start program", being associated with the operation of starting the selected program of the device 100. Hence, in this example, the other process state is here a program started state.

However, it should further be noted that in case the device 100 is not able to start the selected program, e.g. the chamber 140 may not be hot enough for the selected program, etc., the device 100 may enter other further process states, such as, e.g. one or more warning process states, before re-entering the program selected state or entering in the program started state. For the sake of simplicity, however, these process states and their displays views are not described or shown in more detail herein.

Fourth View 340

This fourth view 340 may, for example, be shown during a detected program started state and in response to detecting the change C4.

In the simplified embodiment of FIG. 3, the device 100 is here configured, when being in the detected program selected state, to allow the user of the device 100 to interrupt the ongoing program, e.g. intervene in or cancel an ongoing program. The device 100 comprises a fourth set of graphical interactive user interface objects 340A which are associated with this allowed operation and the detected program started state.

As shown in the fourth view 340, the fourth set of graphical interactive user interface objects 340A may comprise the graphical interactive user interface object, "Cancel", being associated with the operation of interrupting the selected program of the device 100. Here, the fourth view 340 may also comprise a graphical user interface object indicating process time of the started program of the device 100. This graphical user interface object may, for example, comprise a digital clock showing the time remaining of the started program, and a circular figure being filled in percentage of the total program time that has lapsed.

In the fourth view 340, the device 100 indicates, e.g. by means of the indicating unit (or display unit) 112 on the display 130, the fourth set of graphical interactive user interface objects 340A visually differentiated from other graphical interactive user interface objects 340B. In this case, the other graphical interactive user interface objects 340B may comprise the graphical interactive user interface object, "Open door", the graphical interactive user interface object, "Close door", and the graphical interactive user interface object, "Start program". Also, note that the other graphical interactive user interface objects 340B, in this case, may also comprise all other graphical interactive user interface objects not being indicated (displayed) in the fourth view 340.

As can be seen in the fourth view 340, the fourth set of graphical interactive user interface objects 340A are shown as clearly distinctive from the other graphical interactive user interface objects 340B by having heavily marked edges (as indicated by the fully drawn, heavy lines) and bold font, whereas the other graphical interactive user interface objects 340B are either not displayed or have faintly marked edges (as indicated by the dashed lines) and regular font. In some embodiments, the fourth set of graphical interactive user interface objects 330A may preferably comprise a blue color to some extent so as to guide the user onwards.

This translates into the fourth set of graphical interactive user interface objects 340A being perceived as active, whereas the other graphical interactive user interface objects 340B are perceived as inactive. However, as previously described in embodiments above, many modifications and variations are possible for achieving the desired differentiation between the fourth set of graphical interactive user interface objects 340A and the other graphical interactive user interface objects 340B.

When in program started state, the device 100 may, e.g. by means of the detecting unit 111, also detect further changes C5 or C6 in the current process state of the device 100 from the program started state into another process state. In this example, this may e.g. be caused by the device 100 detecting that the on-going program of the device 100 has been: (C5) successfully completed or (C6) not successfully completed. Hence, in this example, the other process state is here a program complete state.

It should further be noted that, when in the program started state, other further process states, such as, one or more alarm process states or warning process states, e.g. due to improper functioning of the device 100, or one or more cancel process states, e.g. when the user has chosen to interrupt an on-going process, may also be entered by the device 100. For the sake of simplicity, however, these process states and their displays views are not described or shown in more detail herein.

Figure 4:
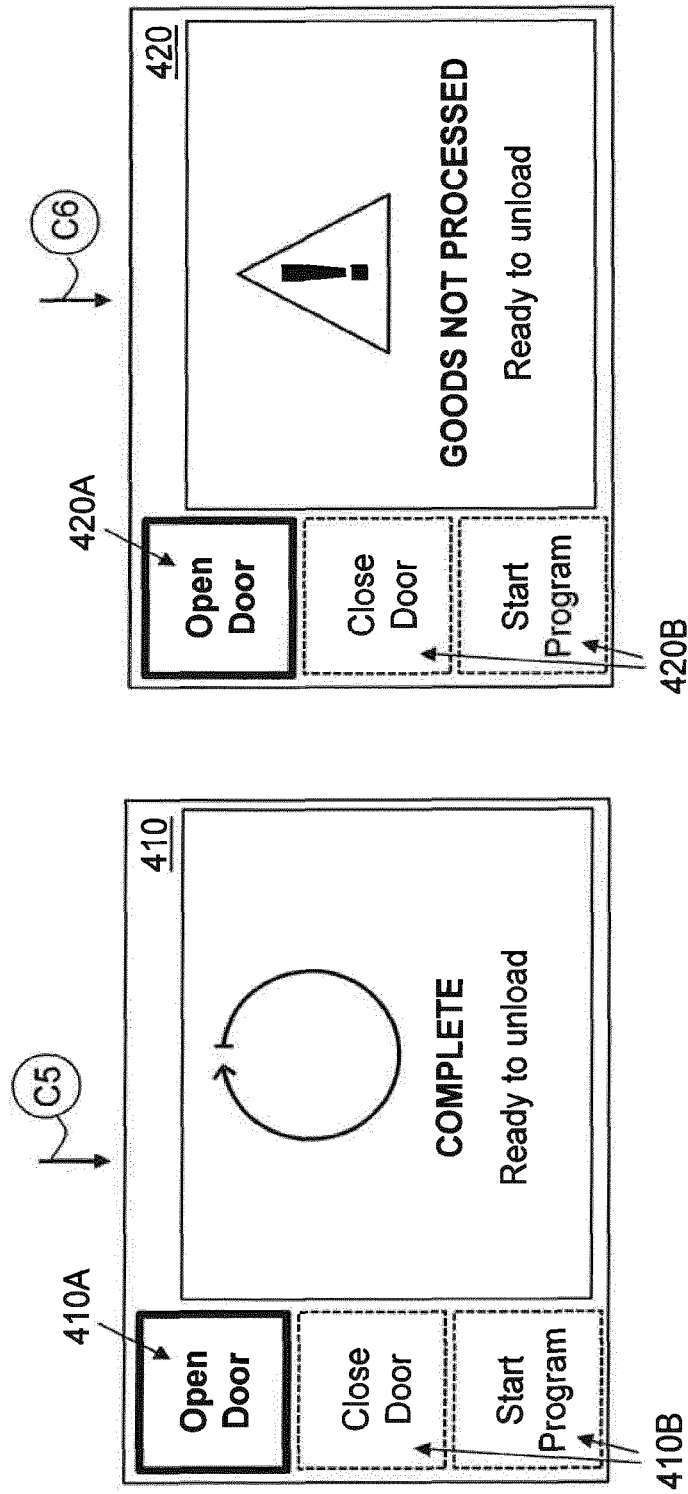
FIG. 4 shows further exemplifying display views comprising graphical interactive user interface objects depicting embodiments of the device for washing, disinfecting and/or sterilizing medical, dental, laboratory and/or pharmaceutical goods.

FIG. 4 shows exemplifying further display views 410, 420 of the display 130 comprising sets of graphical interactive user interface objects 410A, 410B, 420A, 420B according to some embodiments. It should be noted that the embodiments described below are simplified for more clearly demonstrating the principle of the embodiments described herein.

Fifth View 410

This fifth view 410 may, for example, be shown during a detected program complete state and in response to detecting the change C5.

In the simplified embodiment of FIG. 4, the device 100 is here configured, when being in the detected program complete state, to allow the user of the device 100 to open the door 150. The device 100 comprises a fifth set of graphical interactive user interface objects 410A which are associated with this allowed operation and the detected program complete state. As shown in the fifth view 410, the fifth set of graphical interactive user interface objects 410A may comprise the graphical interactive user interface object, "Open door", as previously described. Here, the fifth view 410 may also comprise a graphical user interface object indicating the program has completed successfully.

In the fifth view 410, the device 100 indicates, e.g. by means of the indicating unit (or display unit) 112 on the display 130, the fifth set of graphical interactive user interface objects 410A visually differentiated from other graphical interactive user interface objects 410B. In this case, the other graphical interactive user interface objects 410B may comprise the graphical interactive user interface object, "Close door", and the graphical interactive user interface object, "Start program". Also, note that the other graphical interactive user interface objects 410B, in this case, may also comprise all other graphical interactive user interface objects not being indicated (displayed) in the fifth view 410.

As can be seen in the fifth view 410, the fifth set of graphical interactive user interface objects 410A are shown as clearly distinctive from the other graphical interactive user interface objects 410B by having heavily marked edges (as indicated by the fully drawn, heavy lines) and bold font, whereas the other graphical interactive user interface objects 410B are either not displayed or have faintly marked edges (as indicated by the dashed lines) and regular font. In some embodiments, the fifth set of graphical interactive user interface objects 410A may preferably comprise a blue color so as to guide the user onwards. Also, in some embodiments, a graphical user interface object indicating that the program has been completed successfully, e.g. the goods are now washed, disinfected or sterile, and that the goods are ready to be unloaded from the device 100 may also be displayed. In some embodiments, this graphical user interface object may preferably comprise a green color to clearly indicate to the user that the program completed successfully.

This translates into the fifth set of graphical interactive user interface objects 410A being perceived as active, whereas the other graphical interactive user interface objects 410B are perceived as inactive. However, as previously described in embodiments above, many modifications and variations are possible for achieving the desired differentiation between the fifth set of graphical interactive user interface objects 410A and the other graphical interactive user interface objects 410B.

Sixth View 420

This sixth view 420 may, for example, be shown during a detected program complete state and in response to detecting the change C6.

In the simplified embodiment of FIG. 4, the device 100 is here configured, when being in the detected program complete state, to allow the user of the device 100 to open the door 150. The device 100 comprises a sixth set of graphical interactive user interface objects 420A which are associated with this allowed operation and the detected program complete state. As shown in the sixth view 420, the sixth set of graphical interactive user interface objects 420A may comprise the graphical interactive user interface object, "Open door", as previously described. Here, the sixth view 410 may also comprise a graphical user interface object indicating the program has not been successfully completed, e.g. due to some error occurring during the on-going program of the device 100.

In the sixth view 420, the device 100 indicates, e.g. by means of the indicating unit (or display unit) 112 on the display 130, the sixth set of graphical interactive user interface objects 420A visually differentiated from other graphical interactive user interface objects 420B. In this case, the other graphical interactive user interface objects 420B may comprise the graphical interactive user interface object, "Close door", and the graphical interactive user interface object, "Start program". Also, note that the other graphical interactive user interface objects 420B, in this case, may also comprise all other graphical interactive user interface objects not being indicated (displayed) in the sixth view 420.

As can be seen in the sixth view 420, the sixth set of graphical interactive user interface objects 420A are shown as clearly distinctive from the other graphical interactive user interface objects 420B by having heavily marked edges (as indicated by the fully drawn, heavy lines), whereas the other graphical interactive user interface objects 420B are either not displayed or have a faintly marked edges (as indicated by the dashed lines). In some embodiments, the sixth set of graphical interactive user interface objects 420A may preferably comprise a blue color so as to guide the user onwards. Also, in some embodiments, a graphical user interface object indicating that the program has not been completed successfully, e.g. the goods may not be satisfactory washed, disinfected or sterile, may also be displayed. In some embodiments, this graphical user interface object may preferably comprise a yellow color to clearly indicate to the user that the program did not completed successfully.

This translates into the sixth set of graphical interactive user interface objects 420A being perceived as active, whereas the other graphical interactive user interface objects 420B are perceived as inactive. However, as previously described in embodiments above, many modifications and variations are possible for achieving the desired differentiation between the sixth set of graphical interactive user interface objects 420A and the other graphical interactive user interface objects 420B.

It should further be noted that the positioning, size, and layout of the graphical interactive user interface objects in the sets of graphical interactive user interface objects 310A, 310B, 320A, 320B, 330A, 330B, 340A, 340B, 410A, 410B, 420A, 420B may be arbitrarily selected and adapted to the implementation at hand. Here, the graphical interactive user interface objects are represented by virtual buttons, comprising explanatory text. Naturally, the graphical interactive user interface objects may additionally and/or alternatively comprise explanatory symbols and/or icons. In order to distinguish the graphical interactive user interface objects in the sets 310A, 320A, 330A, 340A, 410A, 420A from other shown information, and from inactive graphical interactive user interface objects in the sets 310B, 320B, 330B, 340B, 410B, 420B not comprised in the set of graphical interactive user interface objects in the sets 310A, 320A, 330A, 340A, 410A, 420A currently indicated in view of the allowed operations of the current process state, the graphical interactive user interface objects in the sets 310A, 320A, 330A, 340A, 410A, 420A may be visualized e.g. with comparably larger and/or bolder fonts, and/or frames, different coloring, intensity, shadowing and the like, as described in embodiments above.

From the exemplifying display views 310, 320, 330, 340, 410, 420 of the display 130 depicted in FIGS. 3-4, some of the advantages of the embodiments described herein may be easily seen.

For example, the graphical interactive user interface object, "Open door", is readily available on the display 130 when the device 100 is in a process state which allows the opening of the door 150 of the device 100. Also, the graphical interactive user interface object, "Close door", is readily available on the display 130 when the device 100 is in a process state which allows the closing of the door 150 of the device 100. This provides e.g. an advantage over other devices for washing, disinfecting and/or sterilizing medical, dental, laboratory and/or pharmaceutical goods that have implemented hard keys for start/stop functions, which thus may be pressed or be perceived as usable by a user of the device 100 even though it is not to be used or usable at a current process state of the device 100.

Furthermore, the graphical interactive user interface object, "Start program", is readily available on the display 130 when the device 100 is in a process state which allows a program of the device 100 to be started. Thus, the user may not accidentally start or initiate a program until the device 100 is in a process state which allows a program of the device 100 to be started.

According to some embodiments, some graphical interactive user interface objects of a set of graphical interactive user interface objects, representing a number of possible different operations for the user, such as, e.g. open the door, close the door and/or start the program, are indicated on the display 130. Simultaneously, some graphical interactive user interface objects in the same set of graphical interactive user interface objects, representing a number of possible different device oriented settings for the user, such as, different programs e.g. sterilization programs, are indicated on the display 130.

In this embodiment, when a user selects one of the graphical interactive user interface objects representing a number of possible different device oriented settings, the visual appearance of at least one of the graphical interactive user interface objects representing a number of possible different operations for the user is visually changed, indicating a new possible operation for the user. In this manner, a user may be guided through possible process states which are available based on the current selected program, process state and/or operation by the user. Other non-available process states based on the current selected program, process state and/or operation can optionally be suppressed by displaying them visually differentiated or by hiding or concealing them from view.

In some embodiments, the process of operating the device 100 comprises a number of process states in each of which only a limited set of operations are allowed and relevant in the context of leading a user of the device (100) in transitioning the device (100) from one process state into another process state, e.g. from the first to the second process state or from the second to the third process state. In the first process state, a fixed amount of graphical interactive user interface objects are displayed on a portion of the display, and in the second process state the same amount of graphical interactive user interface objects is displayed in the same portion of the display, and during the second process state, at least one of the graphical interactive user interface objects displayed is displayed visually differentiated from the graphical interactive user interface objects displayed in the first process state. For example, if in the first process state a first, a second and a third graphical interactive user interface objects are displayed, only one first graphical interactive user interface object is active representing a possible operation for the user. In the second process state, the first graphical interactive user interface object is deactivated from being an available possible operation for the user and the second graphical interactive user interface object is activated representing a second possible operation for the user. Thus, the first graphical interactive user interface object is shown visually differentiated from the second graphical interactive user interface object.

It should also be noted that sterilization (or sterilisation) herein relates to a process that eliminates (removes) or kills microbial life, including transmissible agents (such as fungi, bacteria, viruses, spore forms, etc.) present on a surface, contained in a fluid, in medication, and/or on and/or in a compound such as biological culture media. Sterilization can be achieved by applying heat, chemicals, irradiation, high pressure, and filtration or combinations thereof. Steam sterilization, or autoclaving, involves subjecting goods to steam at a high temperature. Steam sterilization involves the use of saturated steam under pressure and is a non-toxic method for sterilization. Further, steam sterilizers (autoclaves) are available in different sizes for different purposes. Four factors are relevant for the outcome of steam sterilization: steam, pressure, temperature and time.

It should further be noted that a device for washing, disinfecting and/or sterilizing medical, dental, laboratory and/or pharmaceutical goods using a washing, disinfecting and/or sterilizing process, such as described in the embodiments above, should preferably be adapted to operate at a temperature above 100° C., preferably above 120° C., more preferably between 120-140° C. and at suitable pressure, at least above 101.3 kPa. A sterilizer disclosed herein should preferably at least meet the requirement of EN285:2006 and A2:2009, standards used in this field of technology and known to the skilled person in the art.

The sterilization time required varies depending on the goods to be sterilized, sterilization time necessary at a defined temperature will also depend on the goods to be sterilized. Chemical and biological indicators are available for monitoring the sterilization process and to ensure that sterility is achieved. Properly executed steam sterilization will inactivate all fungi, bacteria, viruses and bacterial spores. If not all fungi, bacteria, viruses and bacterial spores can be removed or deactivated, the temperature, time and pressure is selected so that the sterilization device, and the method, has a Sterility assurance level, SAL, of at most 1/1.000.000, preferably lower than 1/1.000.000. SAL is used to describe the probability of a non-sterile unit exiting the device or method after the sterilization process has been completed.

The embodiments herein are not limited to the above described preferred embodiments. Various alternatives, modifications and equivalents may be used. Therefore, the above embodiments should not be construed as limiting.

Additionally, in the claims, the word "comprising" does not exclude other elements or steps, and the indefinite article "a" or "an" does not exclude a plurality.

The invention claimed is:

1. A device for washing, disinfecting and/or sterilizing medical, dental, laboratory and/or pharmaceutical goods, the device comprising:
    a touch screen;
    a chamber for receiving said medical, dental, laboratory and/or pharmaceutical goods;
    a door; and
    processing circuitry and computer executable instructions configured to cause the device to perform a process as follows:
    detecting a first process state of the device;
    indicating permitted ways of operating the device in the first process state to a user by indicating on the touch screen a first set of graphical interactive user interface objects, the first set of graphical interactive user interface objects being associated with the first process state and being visually differentiated on the touch screen from other graphical interactive user interface objects not associated with the first process state, wherein the user can interact with the first set of graphical interactive user interface objects via the touch screen to cause the process of operating the device to change from the first process state to a second process state;
    detecting that the process of operating the device has changed to the second process state; and
    in response to detecting that the process of operating the device has changed to the second process state, indicating permitted ways of operating the device in the second process state to the user by indicating on the touch screen a second set of graphical interactive user interface objects, the second set of graphical interactive user interface objects being associated with the second process state and visually differentiated from other graphical interactive user interface objects not associated with the second process state, wherein the user can interact with the second set of graphical interactive user interface objects via the touch screen to cause the process of operating the device to change from the second process state to a further process state;
    wherein the detecting is performed by the device in response to a user interaction with the device, and/or in response to a detected change in the operation of the device by the device itself;
    wherein the first set of graphical interactive user interface objects and the second set of graphical interactive user interface objects are at least partially different; and
    wherein at least one of the first process state and the second process state is a washing, disinfecting, and/or sterilizing process state of the device.

2. The device according to claim 1, the device being configured wherein the first set and the second set of graphical interactive user interface objects are visually differentiated from the other graphical interactive user interface objects during the first process state and the second process state, respectively, by one or more of the following:
    coloring versus non-coloring;
    a first coloring versus at least one second coloring;
    a first display intensity versus a second display intensity;
    frames versus no frames; and/or
    a first font versus at least one second font.

3. The device according to claim 1, the device configured wherein:
    one of said first process state and said second process state is selected from: an alarm process state and a warning process state.

4. The device according to claim 1:
    wherein the graphical interactive user interface objects include a door open user interface object, the device being configured to open the door in response to the user interacting with the door open user interface object;
    the device being further configured:
    to perform a washing, disinfecting, and/or sterilizing process in response to a user input selecting one of said first set of graphical interactive user interface objects;
    during said washing, disinfecting, and/or sterilizing process, to suppress the door open user interface object, and thereby prevent opening of the door; and
    after the washing, disinfecting, and/or sterilizing process is complete, to emphasize the door open user interface object.

5. The device according to claim 1, the device being configured wherein:
    when the device is in the first process state, graphical interactive user interface objects not associated with the first process state are suppressed on the touch screen; and
    the device ignores user interactions with graphical interactive user interface objects which are suppressed, and maintains the same operating state of the device before and after user interactions with the graphical interactive user interface objects which are suppressed.

6. The device according to claim 1, wherein the device for washing, disinfecting and/or sterilizing medical, dental, laboratory and/or pharmaceutical goods comprises an autoclave.

7. A device for washing, disinfecting and/or sterilizing medical, dental, laboratory and/or pharmaceutical goods, and configured to guide a user of the device through a plurality of process states during operation of the device, comprising:
    a display screen;
    a chamber for receiving said medical, dental, laboratory and/or pharmaceutical goods;
    a door, the door positioned to control access to the chamber; and processing circuitry and computer executable instructions configured to cause the device to perform a process as follows:
displaying on the display screen of the device a plurality of graphical interactive user interface objects associated with the operation of the device;
detecting a first process state of the device;
emphasizing, on the display screen by differential displaying, graphical interactive user interface objects that are associated with the first process state, and suppressing graphical interactive user interface objects that are not associated with the first process state;
receiving a user input selecting one of the plurality of graphical interactive user interface objects associated with the first process state;
in response to said receiving the user input, transitioning the device from the first process state to a second process state; and then
emphasizing, on the display screen by differential displaying, at least one of said plurality of graphical interactive user interface objects that are associated with the second process state, and suppressing graphical interactive user interface objects that are not associated with the second process state;
wherein the first process state and second process state are different operational states of the device with respect to a washing, disinfecting, and/or sterilizing process of the device; and
wherein the graphical interactive user interface objects associated with the first process state and the graphical interactive user interface objects associated with the second process state are at least partially different.

8. The device according to claim 7, the device configured wherein:
user interactions with suppressed graphical interactive user interface objects are ignored.

9. The device according to claim 7, wherein the display screen comprises a touch screen configured for receiving user input, and configured for displaying said plurality of graphical interactive user interface objects.

10. The device according to claim 7, the device configured wherein emphasizing the graphical interactive user interface objects that are associated with the first process state, and suppressing the graphical interactive user interface objects that are not associated with the first process state, includes one or more of:
displaying the graphical interactive user interface objects that are associated with the first process state, and not displaying the graphical interactive user interface objects that are not associated with the first process state;
coloring the graphical interactive user interface objects that are associated with the first process state, and displaying the graphical interactive user interface objects that are not associated with the first process state in grayscale;
displaying the graphical interactive user interface objects that are associated with the first process state in a first coloring, and displaying the graphical interactive user interface objects that are not associated with the first process state in at least one second coloring;
displaying the graphical interactive user interface objects that are associated with the first process state in a first display intensity, and displaying the graphical interactive user interface objects that are not associated with the first process state in a lower second display intensity;
framing the graphical interactive user interface objects that are associated with the first process state, and not framing the graphical interactive user interface objects that are not associated with the first process state; and/or
using a first font for the graphical interactive user interface objects that are associated with the first process state, and using at least one different second font for the graphical interactive user interface objects that are not associated with the first process state.

11. The device according to claim 7, the device configured wherein the plurality of graphical interactive user interface objects comprises:
a door open object;
a door close object; and
a plurality of objects for selecting among a plurality of respective washing, disinfecting and/or sterilizing programs.

12. The device according to claim 7, the device configured wherein:
the plurality of graphical interactive user interface objects comprises an object for starting a washing, disinfecting, or sterilizing program; and
wherein said object for starting a washing, disinfecting, or sterilizing program is suppressed when the device detects that the door is in an open state.

13. The device according to claim 7, wherein the device configured to transition to a different process state in response to detecting that the door has been closed.

14. The device according to claim 7, the device configured wherein:
the plurality of graphical interactive user interface objects associated with the first process state comprises a start program object;
to transition to the second process state in response to a user interacting with the start program object;
to initiate a washing, disinfecting, or sterilizing program in response to the user interacting with the start program object, the washing, disinfecting, or sterilizing process being the second process state; and
wherein a door open object is suppressed in the second process state.

15. The device according to claim 7, wherein
the plurality of graphical interactive user interface objects comprises a plurality of program objects for selecting among a plurality of programs, said programs comprising different washing, disinfecting and/or sterilizing programs; and
in response to a user selecting a program object, the device is configured to present at least one of program parameters and program settings for the corresponding program on the display screen.

16. The device according to claim 7, the device configured wherein:
the second process state comprises a washing, disinfecting, or sterilizing process;
the device enters a third process state in response to completion of the washing, disinfecting, or sterilizing process;
the device emphasizes, on the display screen, graphical interactive user interface objects that are associated with the third process state, and suppresses graphical interactive user interface objects not associated with the third process state; and wherein the graphical interactive user interface objects associated with the second process state and with the third process state are at least partially different.

17. The device according to claim 7, the device configured wherein:
the plurality of graphical interactive user interface objects includes a door open user interface object, the device being configured to open a door in response to the user interacting with the door open user interface object;
the door open user interface object is suppressed during washing, disinfecting, and/or sterilizing processes, thereby preventing opening of the door; and
the door open user interface object is emphasized after completion of said washing, disinfecting, and/or sterilizing processes.

18. The device according to claim 7, wherein the device for washing, disinfecting and/or sterilizing medical, dental, laboratory and/or pharmaceutical goods comprises an autoclave, a washer, a washer disinfector, a sterilizer, or a drying cabinet.

19. A device for washing, disinfecting and/or sterilizing medical, dental, laboratory and/or pharmaceutical goods:
wherein the device for washing, disinfecting and/or sterilizing medical, dental, laboratory and/or pharmaceutical goods is an autoclave, a sterilizer, or a washer-disinfector, the device comprising:
a touch screen;
a chamber for receiving said medical, dental, laboratory and/or pharmaceutical goods;
a door; and
processing circuitry and computer executable instructions configured to cause the device to perform a process as follows:
displaying on the touch screen of the device a plurality of graphical interactive user interface objects associated with the operation of the device;
detecting a first process state of the device;
emphasizing, on the touch screen by differential displaying, graphical interactive user interface objects that are associated with the first process state, and suppressing graphical interactive user interface objects that are not associated with the first process state;
receiving a user input selecting one of the graphical interactive user interface objects associated with the first process state;
in response to said receiving the user input, transitioning the device from the first process state to a second process state; and
emphasizing, on the touch screen by differential displaying, at least one of said plurality of graphical interactive user interface objects that are associated with the second process state, and suppressing graphical interactive user interface objects that are not associated with the second process state;
wherein the first process state and second process state are different operational states of the device; and
wherein the graphical interactive user interface objects associated with the first process state and the graphical interactive user interface objects associated with the second process state are at least partially different.

20. The device according to claim 19, the device configured wherein:
the plurality of graphical interactive user interface objects comprises: a door open object, a door close object, a start program object, and a plurality of objects for selecting among a plurality of different respective washing, disinfecting and/or sterilizing programs;
the door open object is suppressed when a washing, disinfecting, and/or sterilizing program is in progress; and
the start program object is suppressed when the door is open.

21. The device according to claim 19:
wherein the device is a sterilizer configured for sterilizing medical, dental, laboratory, and/or pharmaceutical goods held in the chamber by applying one or more chemical sterilant therein.

* * * * *